United States Patent
Raymond et al.

(10) Patent No.: US 7,753,912 B2
(45) Date of Patent: Jul. 13, 2010

(54) TISSUE DISTRACTION DEVICE

(75) Inventors: Spanky A. Raymond, Uniontown, OH (US); Frank S. Bono, Collierville, TN (US); Thomas G. Wilson, Guilford, CT (US); Joseph Logan, Trumbull, CT (US); Steven J. Wysocki, Stratford, CT (US)

(73) Assignee: Spine Wave, Inc., Shelton, CT (US)

( * ) Notice: Subject to any disclaimer, the term of this patent is extended or adjusted under 35 U.S.C. 154(b) by 1153 days.

(21) Appl. No.: 10/813,819

(22) Filed: Mar. 31, 2004

(65) Prior Publication Data
US 2005/0187559 A1   Aug. 25, 2005

Related U.S. Application Data

(60) Provisional application No. 60/459,036, filed on Mar. 31, 2003.

(51) Int. Cl.
A61F 2/28   (2006.01)

(52) U.S. Cl. ............................................ 606/90; 606/99

(58) Field of Classification Search .................. 606/61, 606/90, 99, 143; 623/17.11
See application file for complete search history.

(56) References Cited

U.S. PATENT DOCUMENTS

| | | | |
|---|---|---|---|
| 3,486,505 A | 12/1969 | Morrison | |
| 4,478,220 A * | 10/1984 | Di Giovanni et al. | 606/143 |
| 4,524,766 A | 6/1985 | Petersen | |
| 4,624,254 A * | 11/1986 | McGarry et al. | 606/143 |
| 4,736,768 A | 7/1988 | Lipovsck et al. | |
| 5,190,560 A * | 3/1993 | Woods et al. | 606/137 |
| 5,431,658 A | 7/1995 | Moskovich | |
| 5,522,899 A | 6/1996 | Michelson | |
| 5,571,109 A | 11/1996 | Bertagnoli | |
| 5,702,454 A | 12/1997 | Baumgartner | |
| 5,782,844 A * | 7/1998 | Yoon et al. | 606/139 |
| 5,827,289 A | 10/1998 | Reiley et al. | |
| 5,997,552 A * | 12/1999 | Person et al. | 606/139 |
| 6,159,211 A | 12/2000 | Boriani et al. | |
| 6,273,898 B1 * | 8/2001 | Kienzle et al. | 606/142 |
| 6,488,710 B2 | 12/2002 | Besselink | |
| 6,595,998 B2 * | 7/2003 | Johnson et al. | 606/90 |
| 6,656,178 B1 * | 12/2003 | Veldhuizen et al. | 606/61 |
| 6,695,854 B1 * | 2/2004 | Kayan et al. | 606/143 |
| 2005/0124999 A1 * | 6/2005 | Teitelbaum et al. | 606/99 |

\* cited by examiner

*Primary Examiner*—Thomas C Barrett
*Assistant Examiner*—Nicholas Woodall
(74) *Attorney, Agent, or Firm*—Maginot, Moore & Beck LLP

(57) ABSTRACT

An apparatus and method for distracting, in a given direction, and supporting two tissue surfaces is disclosed using a column of wafers. The column of wafers is oriented so as to expand in the given direction as the wafers are consecutively added to the column. A wafer insertion apparatus includes a wafer cartridge configured to carry a stack of wafers to be inserted into the space, a track assembly including a first track for carrying a wafer toward the space, a second track and means for preventing retrograde movement of a wafer within the first track, an advancer/pusher mechanism slidably disposed within the second track and operable on a wafer within the first track to advance the wafer along the first track, and an advancement gun operably coupled to the advancer/pusher mechanism to propel the mechanism along the second track.

12 Claims, 15 Drawing Sheets

TISSUE DISTRACTION DEVICE

REFERENCE TO RELATED APPLICATION

This application claims priority to provisional application No. 60/459,036, filed on Mar. 31, 2003, in the name of the present inventors. The disclosure of this provisional application No. 60/459,036 is incorporated herein by reference.

FIELD OF THE INVENTION

The present invention involves the field of surgery, and particularly to the field of orthopaedic surgery, surgical instruments and methods of using the same. The invention has particular application in distracting and supporting tissue surfaces, such as bone surfaces.

BACKGROUND OF THE INVENTION

A variety of physical conditions involve two tissue surfaces that, for treatment of the condition, need to be distracted from one another and then supported away from one another. Such distraction may be to gain exposure to select tissue structures, to apply a therapeutic pressure to select tissues, to return tissue structures to their anatomic position and form, or in some cases to deliver a drug or growth factor to alter, influence or deter further growth of select tissues. Depending on the condition being treated, the tissue surfaces may be opposed or contiguous and may be bone, skin, soft tissue, or a combination thereof. An optimal treatment method includes distracting and supporting the tissue surfaces simultaneously.

A minimally invasive distraction and support device would have significant application in orthopaedic surgical procedures, including acute and elective procedures to treat bone fractures and degenerative changes of the skeletal system and including vertebral compression fractures, interbody fusion, vertebral disc augmentation or replacement, and other compression fractures including, but not limited to tibial plateau compression fractures, calcaneous compression fractures, distal tibia fractures, distal radius (wrist) fractures, crushed or fractured orbit and orthopaedic oncology. Further, a minimally invasive distraction and support device would have application in non-orthopaedic surgical procedures in plastic surgery (for example facial reconstruction), gastrointestinal surgery and urological surgery (for example the treatment of incontinence).

One technique used to treat vertebral compression fractures is injection of bone filler into the fractured vertebral body. This procedure is commonly referred to as percutaneous vertebroplasty. Vertebroplasty involves injecting bone filler (for example, bone cement) into the collapsed vertebra to stabilize and strengthen the crushed bone. In this procedure, lower viscosities and higher pressures tend to disperse the bone filler throughout the vertebral body. However, such conditions dramatically increase the risk of bone filler extravasation from the vertebral body.

Kyphoplasty is a modified vertebral fracture treatment that uses one or two balloons, similar to angioplasty balloons, to attempt to reduce the fracture and restore vertebral height prior to injecting the bone filler. Two balloons are typically introduced into the vertebra via bilateral transpedicular cannulae. The balloons are inflated to reduce the fracture. After the balloon(s) is deflated and removed, leaving a relatively empty cavity, bone cement is injected into the vertebra. In theory, inflation of the balloons restores vertebral height. However, it is difficult to consistently attain meaningful height restoration. It appears the inconsistent results are due, in part, to the manner in which the balloon expands in a compressible media and the structural orientation of the trabecular bone within the vertebra.

A tibial plateau fracture is a crushing injury to one or both of the tibial condyles resulting in a depression in the articular surface of the condyle. In conjunction with the compression fracture, there may be a splitting fracture of the tibial plateau. Appropriate treatment for compression fractures depends on the severity of the fracture. Minimally displaced compression fractures may be stabilized in a cast or brace without surgical intervention. More severely displaced compression with or without displacement fractures are treated via open reduction and internal fixation.

Typically, the underside of the compression fracture is accessed either through a window cut (a relatively small resection) into the side of the tibia or by opening or displacing a splitting fracture. A bone elevator is then used to reduce the fracture and align the articular surface of the tibial condyle. A fluoroscope or arthroscope may be used to visualize and confirm the reduction. Bone filler is placed into the cavity under the reduced compression fracture to maintain the reduction. If a window was cut into the side of the tibia, the window is packed with graft material and may be secured with a bone plate. If a splitting fracture was opened to gain access, then the fracture is reduced and may be stabilized with bone screws, bone plate and screws, or a buttress plate and screws. Both of these methods are very invasive and require extensive rehabilitation.

Spinal fusion is most frequently indicated to treat chronic back pain associated with instability or degenerative disc disease that has not responded to less invasive treatments. Fusion is also prescribed to treat trauma and congenital deformities. Spinal fusion involves removal of the spinal disc and fusing or joining the two adjacent vertebrae. The primary objective for patients suffering from instability is to diminish the patient's pain by reducing spinal motion.

Spinal fusions are generally categorized into two large groups: instrumented and non-instrumented. In non-instrumented procedures, the physician removes tissue from the unstable disc space and fills it with some form of bone graft that facilitates the fusion of the two adjacent vertebral bodies. Instrumented procedures are similar to non-instrumented procedures, except that implants (generally metallic) are also applied to further stabilize the vertebrae and improve the likelihood of fusion.

In all interbody surgical approaches, a relatively large opening is made in the annulus. The nuclear material is removed and the end plates are decorticated to facilitate bony fusion. Overall, the use of interbody devices has resulted in mixed clinical outcomes. Placement of a fixed height device presents challenges in proper tensioning of the annulus. For these and other reasons, there is concern over long-term stability of interbody devices and fusion mass.

A need remains for a system and method for distracting or elevating adjacent tissues that is minimally invasive and more easily implemented. Moreover, the system and method should provide a simplified capability for quantifying and controlling the amount of distraction. The system and method should also permit additional augmentation of the distraction site.

SUMMARY OF THE INVENTION

The invention provides a combination of a temporary or long term implantable device and instrumentation to place the device, in which tissue surfaces are distracted along an axis to enable access to the space between the tissues. Generally, the invention provides wafers for stacking upon one another to provide an axially extending column to distract and support tissue surfaces. While a primary use of the invention is to reduce and stabilize vertebral compression fractures, the invention may be used in any situation where it is desirable to distract two tissue surfaces. The tissue may be bone, skin, soft tissue, or combinations thereof. Further, the surfaces may be opposed surfaces of contiguous elements or surfaces of opposed elements. Thus, the invention may be used to treat vertebral compression fractures, for replacement of vertebral discs, as an interbody fusion device, wedge opening high tibial osteotomy, tibial tuberosity elevation, as well as for treating other compression fractures including, but not limited to tibia plateau fractures, calcaneous, distal tibial fractures, or distal radius (wrist) fractures. The invention may also be used for restoring the floor of the orbit, for elevating soft tissue in cosmetic applications, or in incontinence applications as a urethral restrictor. Alternately, the invention may be used in similar veterinary applications.

The terms "vertical", "up", etc., are occasionally used herein for ease of understanding, and these terms should be taken in reference to the vertebrae of a standing patient. Thus, "vertical" refers generally to the axis of the spine. We may also utilize mutually perpendicular "X", "Y" and "Z" axes to describe configurations and movement, with the Z-axis being the axis of the column of wafers, that is, the direction in which this column grows as wafers are added sequentially to it. The X-axis refers to the axis extending generally in the direction of movement of each wafer as it is advanced to a position beneath a preceding wafer, and the Y-axis is perpendicular to both the X- and Z-axes. The wafers are sometimes described with reference to permitted degrees of freedom or restraint when they are placed in a column. It should be understood that these permitted degrees of freedom or restraint refer to the permitted or restrained movement of one wafer with respect to an adjacent wafer along one or more of the three axes, and the permitted or restrained rotation between adjacent wafers about one or more of these axes.

The distraction device includes a plurality of stackable wafers designed for insertion between tissue surfaces to form a column. The wafer column is assembled in vivo to provide a distraction force as well as support and stabilization of the distracted tissue. Preferably, the wafers place distraction force in one direction only and thus provide directional distraction. The distraction device may be permanently implanted, in which case the wafer column may be used alone or in conjunction with a bone filler material. Alternately, the distraction device may be used temporarily to manipulate tissues and then removed.

In use, the wafers are preferably stacked between two tissue surfaces as they are implanted, thereby distracting and supporting the tissue surfaces simultaneously. In the vertebral compression fracture application, it is preferable to distract along the Z-axis (along the axis of the spine) to restore vertebral height. However, in other applications, it may be preferable to provide distraction in a different direction. The features of a wafer and a column of wafers will be described relative to position and direction. The top of a wafer or the top of the column is defined as the face of the wafer or column in the direction of distraction. The bottom of a wafer or the bottom of the column is defined as the face opposite the top face. In similar fashion, above and below a wafer or column implies along the top and bottom of the wafer or column, respectively. Each wafer has a leading edge that enters the forming column first and a trailing edge opposite the leading edge. The sides of the wafer are adjacent the leading and trailing edges and the top and bottom faces of the wafer. In general, the sides are longer than the leading and trailing edges, however the sides may be shorter than the leading and trailing edges. The axis of the column is defined as a line parallel to the direction of distraction.

In order to place the wafers between the tissue surfaces, a wafer insertion apparatus is positioned within the surgical site with access at its distal tip to the tissue surfaces to be distracted and supported. In one embodiment, a wafer is placed on the track and a plunger is used to advance the wafer to the distal end of the track. This is repeated with consecutive wafers until a column of sufficient height is created per physician discretion. After the wafer(s) have been inserted, the insertion apparatus is removed. The distal end of the insertion apparatus may be manufactured from the same material as the wafers and/or be detachable. In this embodiment, the distal end of the insertion instrument would be detached after placing the wafer column, and the instrument removed.

In another embodiment, the wafer insertion apparatus can be configured for one-hand operation. The wafer insertion apparatus includes an advancement gun assembly that is configured to receive a replaceable wafer cartridge. The cartridge carries a number of wafers to be sequentially inserted into the distraction space by the wafer insertion apparatus. Preferably, the cartridge is biased, meaning that constant pressure is applied to the last wafer of the stack to continually advance wafers to the discharge end of the cartridge. The gun assembly includes a manually operable trigger that operates a linkage mechanism to advance a wafer pusher.

In certain embodiments, the wafer insertion apparatus includes a dual track assembly mounted to the advancement gun assembly. The dual track assembly includes a top track and a bottom track with a wafer "stay" that prevents retrograde motion of a wafer on the way to the distraction site. The top track serves as a carrier for traversing a series of wafers from the cartridge to a delivery or discharge end of the track assembly. The bottom track accepts an individual wafer from the top track at an introduction end of the track assembly and place that wafer in proper position before being advanced or pushed into the distraction site. Wafer stays hold the position of wafers in transit within the track assembly as the pusher and advancing mechanisms are retracted for a subsequent firing.

The wafer insertion apparatus can further include a wafer finger advancer and pusher mechanism. The finger advancer incrementally conveys each wafer one by one with every squeeze of the trigger of the advancement gun assembly. With every stroke of the trigger, the finger advancer advances each wafer within the track assembly incrementally farther down the track to the track tip. In certain embodiments, the finger advancer can include a series of raised fingers or prongs that engage the bottom rear of each wafer.

The pusher mechanism preferably resides within the bottom track and is configured to push a wafer positioned within the bottom track into the distraction site. The pusher mechanism is also actuated by movement of the trigger of the advancement gun assembly. The pusher is preferably coupled to the finger advancer so that they move in unison.

The top track and bottom track are coupled so that the channels defined by the two tracks intersect adjacent the discharge end of the track assembly. The top track is provided with means for diverting a wafer traveling along the wafer channel of the top track into a pusher channel of the bottom track. In one embodiment, the means for diverting includes a spring finger mounted within the wafer channel and configured to guide a wafer into the pusher channel as it is advanced along the wafer channel.

The present invention provides an apparatus for sequentially inserting wafers into a body space that incrementally advances the wafers to be discharged into the body space. One benefit of the invention is that it prevents retrograde movement of the wafers as they are advanced toward the body space. A further benefit is that the wafers can be provided in a removable and replaceable cartridge without disturbing the apparatus or its engagement with the body space.

BRIEF DESCRIPTION OF THE DRAWINGS

FIG. 8 is an exploded view of the wafer cartridge component of the wafer insertion apparatus shown in FIG. 7

DESCRIPTION OF THE PREFERRED EMBODIMENTS

Figure 1:
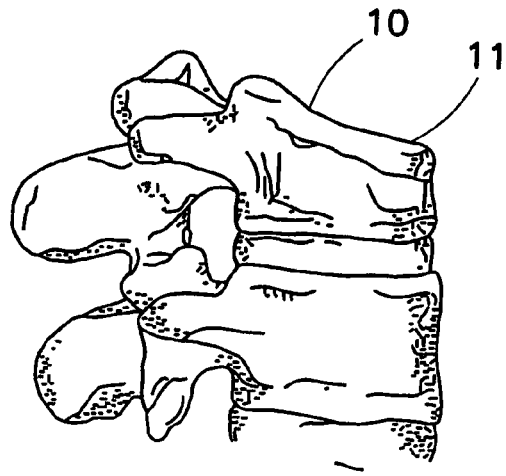
FIG. 1 shows a vertebral body having a compression fracture displacing its superior and anterior edge.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
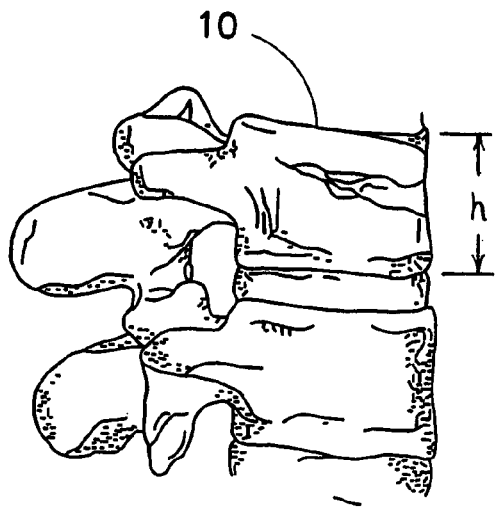
FIG. 2 shows a vertebral body, following treatment of a compression fracture.

The invention provides a combination of an implantable distraction device and instrumentation to place the device. The distraction device is detailed in this section by its application to the vertebral compression fracture. FIG. 1 shows a vertebral body 10 having a compression fracture displacing its superior and anterior edge 11. FIG. 2 shows a vertebral body 10 wherein the height has been restored.

In accordance with the present invention, a plurality of stackable wafers can be provided for insertion between two tissues and can be delivered to a surgical site along an axis transverse to the axis of distraction. Multiple wafer insertions result in a column of wafers at the surgical site that simultaneously distracts and supports the two tissues.

The wafers may be formed from a solid form of bone filler material, and/or any other suitable material such as, but not limited to, implantable grade alloys, medical grade composites, medical grade polymers, ceramics, hydrogels and resorbable polymers. The wafers may be dense or porous, while porous wafers may be filled with resorbable polymers, drug therapies or osteoinductive agents.

Figure 3:
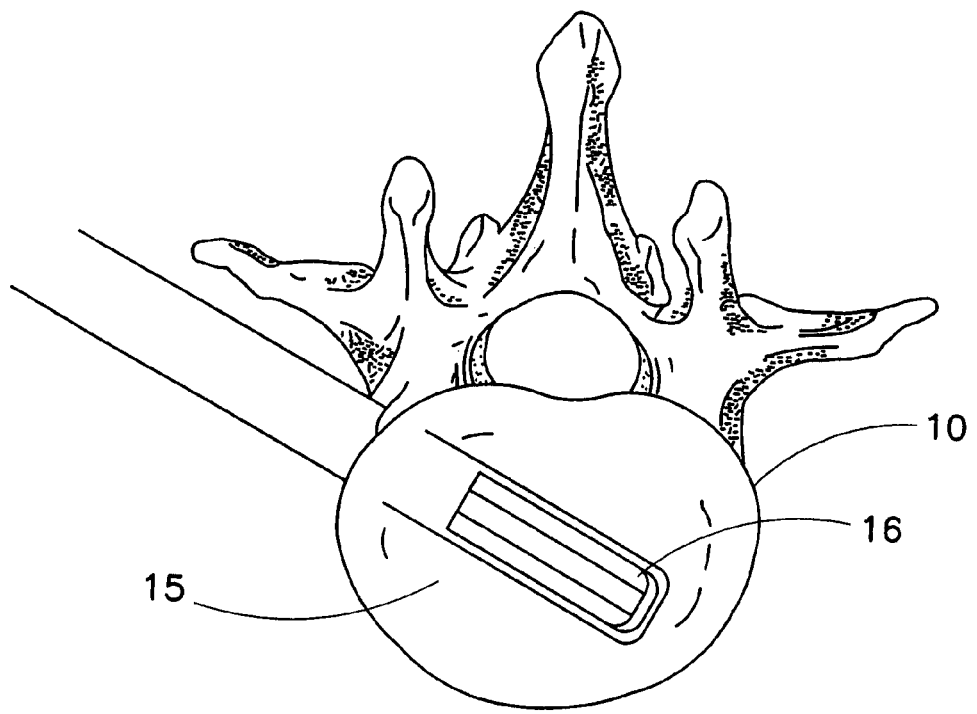
FIG. 3 illustrates a plan view of a distraction device insertion apparatus according to an embodiment of the invention, placed within a vertebral body shown in cross-section.
Figure 4:
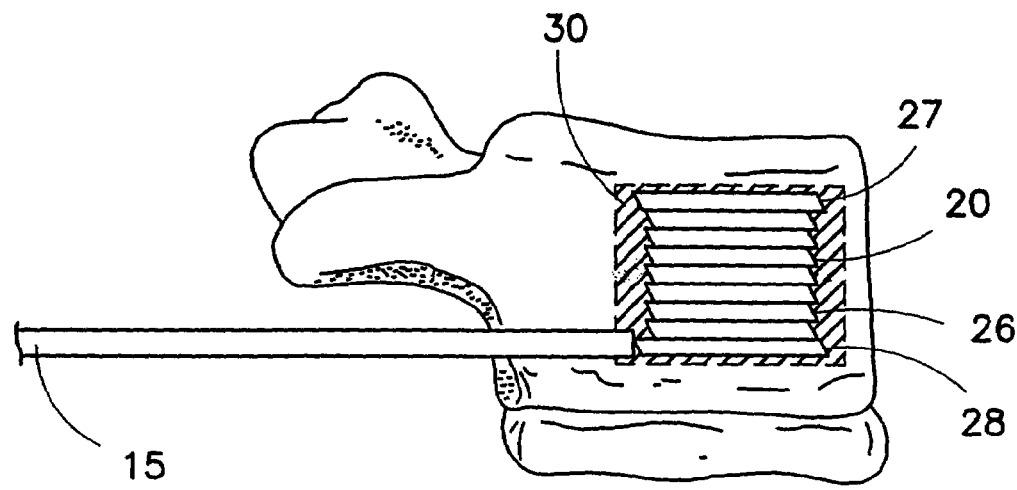
FIG. 4 shows a plan view of a further configuration of distraction device being deployed within a vertebral body, shown in sectional view.

The present invention provides that the wafer column is formed in vivo by using a wafer insertion apparatus. FIG. 3 illustrates the distal or discharge end portion 16 of a wafer insertion apparatus 15 placed within a vertebral body 10 with a wafer 18 positioned distally on the wafer insertion apparatus 15. During implantation, a plurality of such wafers 18 are stacked to form a column to restore vertebral height, such as the column 20 depicted in FIG. 5.

Consecutive wafer insertions result in a column of wafers at the surgical site. In one embodiment, the trailing edge of a wafer can be beveled or otherwise configured to guide the next wafer under the first. For instance, the wafer 22, depicted in FIG. 5, includes a beveled leading edge 23. This beveled edge 23 facilitates guiding the wafer under the trailing edge 24 of a preceding wafer 22. The trailing edge is correspondingly beveled to guide the subsequent wafer underneath.

The wafers 22 can have a variety of configurations and dimensions depending upon the particular surgical application. For instance, for vertebral compression fracture applications, exemplary wafer dimensions range as follows:

Wafer length between 5 mm and 50 mm;
Wafer width between 2 mm and 16 mm;
Wafer thickness between 0.2 mm and 6 mm; and
Curved wafer radii between 10 mm and 500 mm.

These dimensions are provided only as guidelines and any suitable dimensions may be used. Furthermore, the dimensions of the wafer will likely vary widely when the wafers are used in other applications, such as, for example, treating tibial plateau fractures.

In certain applications, it may be beneficial for the wafers to be secured to one another after insertion. Any suitable method for securing the wafers to one another as known by those skilled in the arts may be used. Wafers may be secured to one another by means of an adhesive bond, a chemical bond, and/or a mechanical interlock (as described above). Applying a generic fluent adhesive, for example cyanoacrylate, into the cavity surrounding the column provides adhesive bonding. The fluent adhesive hardens and locks the wafers.

The wafers may also include tunnels, grooves, or holes to facilitate movement of bone filler or other fluent materials through the wafer column into the surrounding bone. Further, openings may be provided through the wafers to allow communication between the tunnels, grooves, or holes or adjacent wafers. In any configuration, bone filler material injected into the wafer column would then flow through the column, fully encapsulating the wafers and better bonding the wafers to the bone filler. Further details of suitable wafers are disclosed in U.S. Pat. No. 6,595,998 (the '998 patent), entitled "Tissue Distraction Device", which issued on Jul. 22, 2003, to the assignee of the present invention. The disclosure of this '998 patent is incorporated herein by reference.

Figure 5:
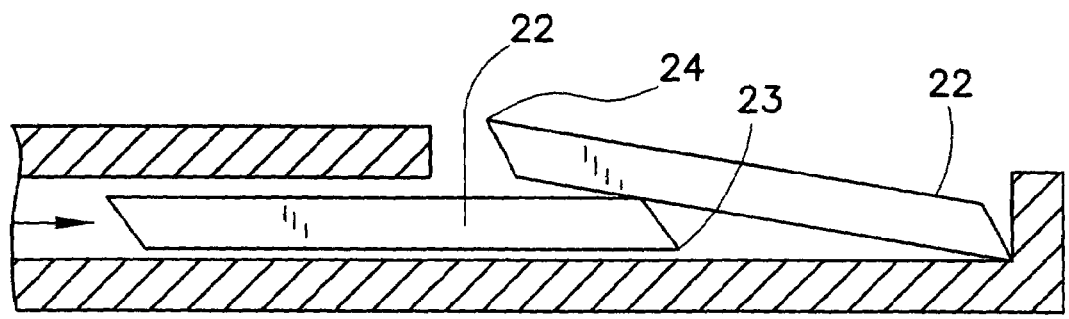
FIG. 5 illustrates a cross-sectional view of the insertion apparatus of FIG. 3 deploying a distraction device according to an embodiment of the present invention.

In a clinical application, the wafers are inserted such that consecutive wafer insertions form a column 20, as shown in FIG. 5. The wafers in the column can be equally sized wafers, such as the intermediate wafers 26. Alternatively or in addition, the column can include larger top and bottom wafers 27, 28, respectively, to provide a larger surface area over which to distribute loads. Moreover, the larger wafers create a space or channel 30 between the edges of the intermediate wafers 26 and the surrounding tissue. This channel provides a path around the interspaced wafers through which a bone filler or other fluent material may flow to fully encapsulate the wafers and to interdigitate with surrounding tissue.

A wafer insertion apparatus is provided as part of the invention to deliver the wafers to the surgical site and to form a column of wafers. In one embodiment, the wafer insertion apparatus applies a force along the X-axis (the axis of insertion) to a wafer that is to be added to the column. As previously described, the wafers may be configured with beveled ends to facilitate growth of the column along the Z-axis (the vertical axis through the wafers) as the additional wafer is inserted.

Numerous variations of the wafer insertion apparatus are possible, the embodiments generally including, but not limited to, a track, a plunger, and a cartridge. The wafer insertion apparatus is comprised of a track, which is a long narrow channel through which wafers pass when placed into the wafer column. A plunger generally advances wafers down the track. Multiple wafers can be housed in a cartridge of the wafer insertion apparatus for advancement down the track. Preferably included is a mechanism for feeding subsequent wafers into the track in front of the plunger. Further, the track is configured for removal from the surgical site while leaving the wafer column intact.

Figure 6:
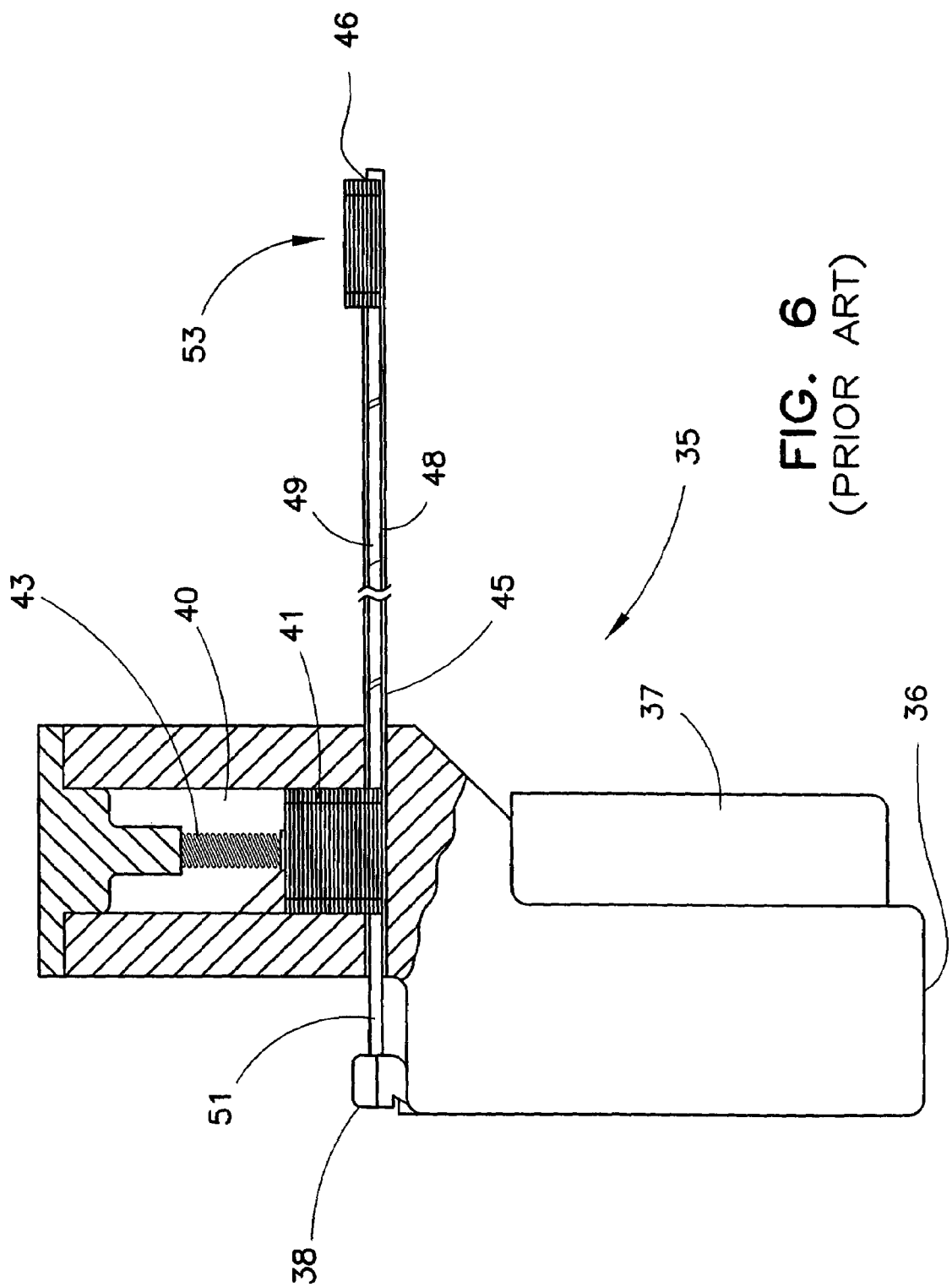
FIG. 6 shows a sectional view of an insertion apparatus according to one embodiment of the present invention.

One embodiment of a wafer insertion apparatus 35 described in the '998 patent is illustrated in FIG. 6. The handle 36 may be gripped to position the wafer insertion apparatus 35. The wafer insertion apparatus has, at its proximal end 38, a magazine 40 containing wafers 41. The wafers 41 may be stacked in the magazine 40 with a top surface of one wafer supporting the bottom surface of an adjacent wafer. The handle 36 is equipped with a trigger 37 for forcing wafers out of the magazine 40. Optionally, the magazine 40 is equipped with a spring 43 to load wafers 41 along a track 45 of the inserter 35. The track 45 extends from the magazine 40 to the surgical site at its distal end 46. As they enter the wafer track 45, the wafers 41 are aligned with the leading edge of one wafer adjacent the trailing edge of a preceding wafer. The track 45 in the wafer insert 35 shown in FIG. 6 includes a lower cavity 48 and an upper cavity 49. A plunger 51 extends through the lower cavity 48 while the wafers 41 are aligned along the upper surface of the plunger. An opening is provided along the top surface of the lower cavity 48 at the distal end 46 of the track 45 to accommodate a wafer. Thus, as the plunger is retracted past the trailing edge of the furthest distal wafer, the wafer drops into the lower cavity. The plunger pushes the wafer distally to form a column of wafers 53.

Figure 7:
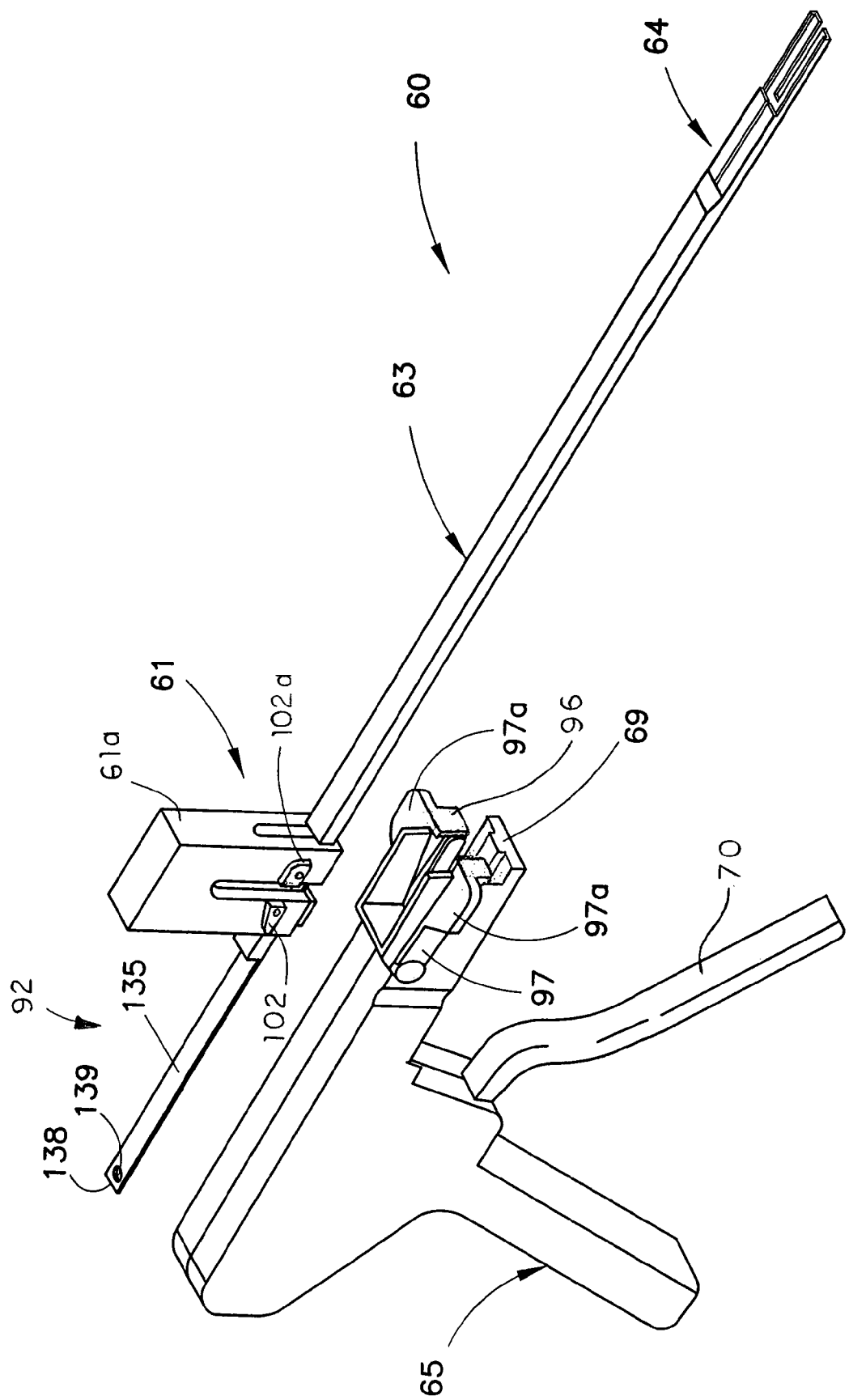
FIG. 7 is a perspective, partially exploded view of a wafer insertion apparatus in accordance with a further embodiment of the invention.

In one embodiment of the invention, a wafer insertion apparatus 60 includes a wafer cartridge 61, a track assembly 63 and an advancement gun 65, as shown in FIG. 7. Referring to the exploded view in FIG. 8, the advancement gun 65 includes left and right housings 67, 68 that can be coupled together in a known manner. Preferably, the housings are formed of a high-density plastic material that can be molded to define various interior and exterior features. The housings support a manual trigger 70 that is pivotably mounted to the housings 67, 68 by a pivot pin 71. The trigger 70 includes a manual grip 72 that is accessible outside the housings, and a lever arm 73 that operates within the housing. The lever arm 73 includes a return spring tab 74, seen best in FIG. 11, which provides a connection point for a return spring 76. The return spring 76 can be mounted within the handle 78 to apply a restorative force to the trigger 70 after it has been manually depressed and released.

Figure 11:
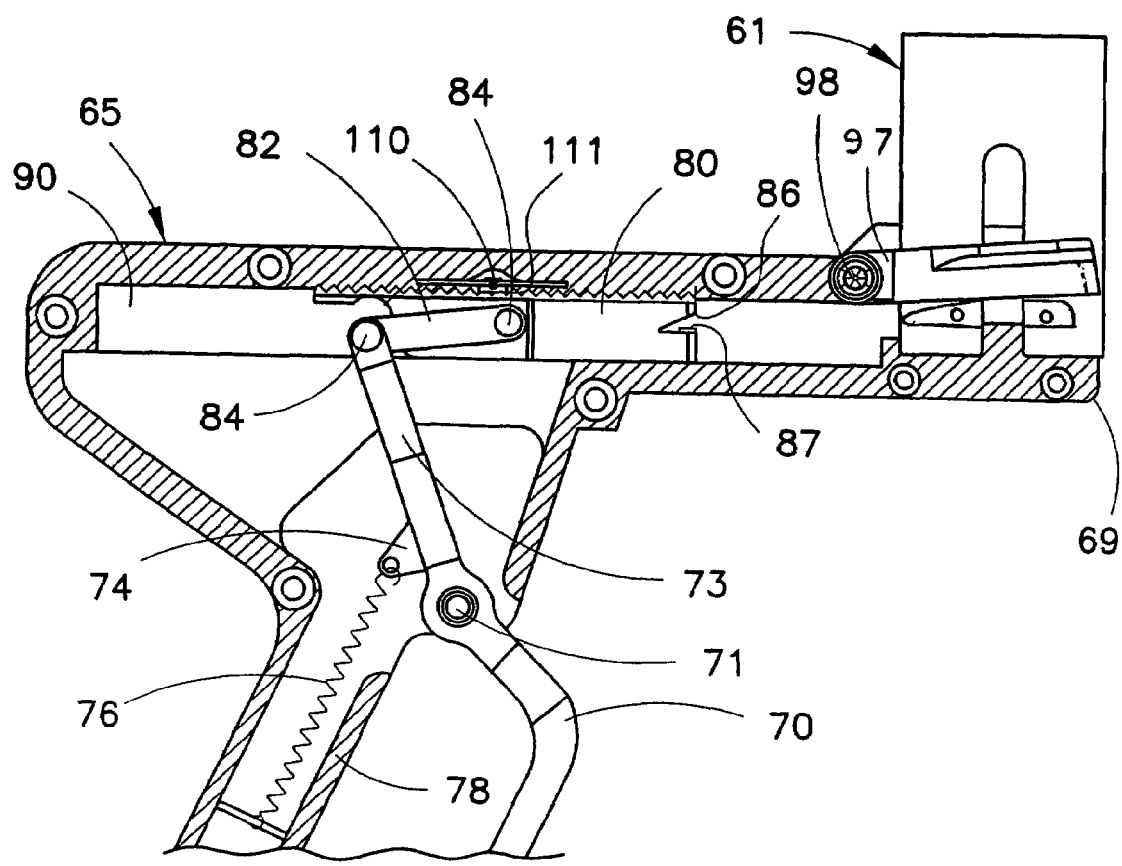
FIG. 11 is an enlarged side cut-away view of the wafer insertion apparatus shown in FIG. 7.
Figure 12:
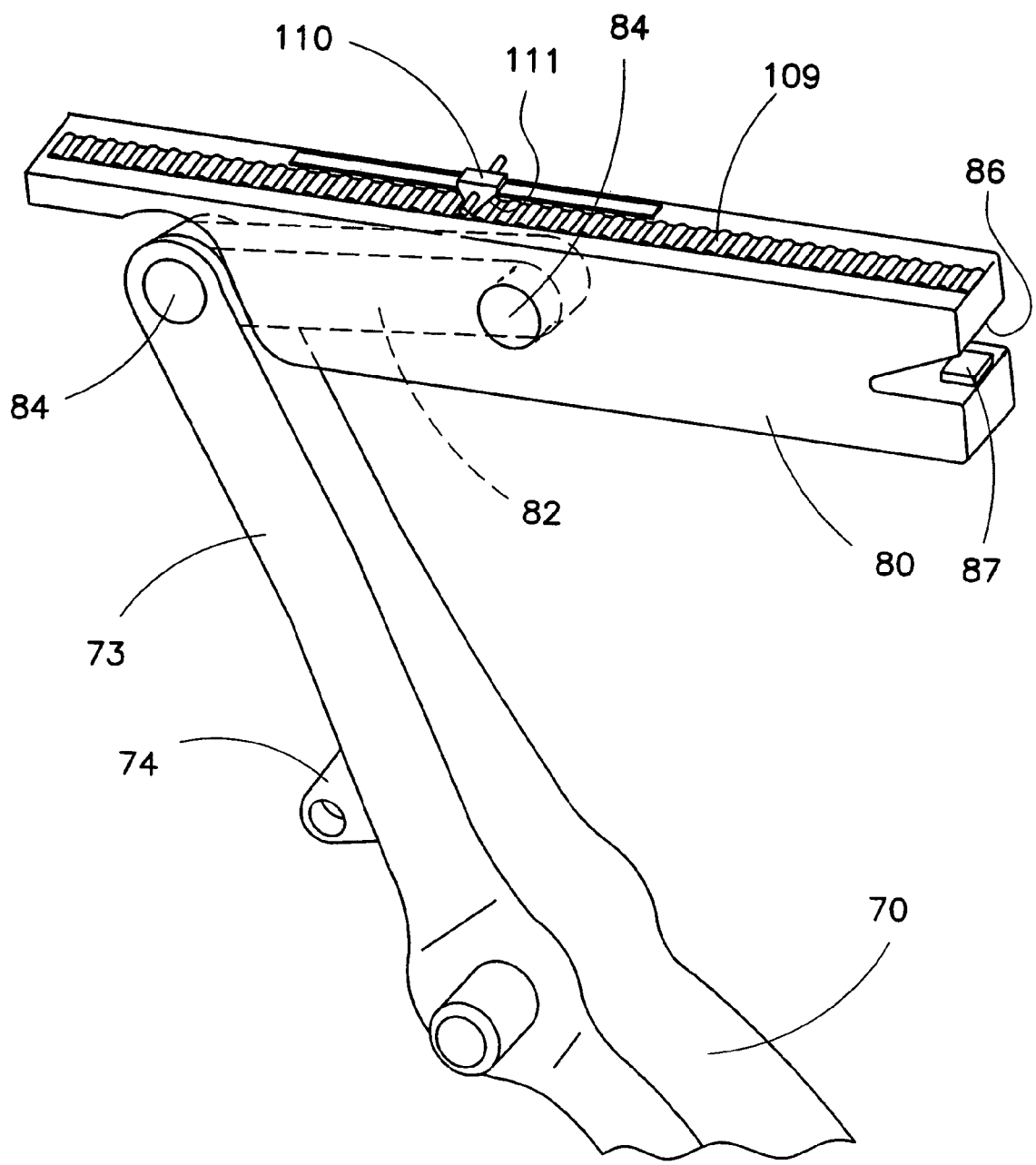
FIG. 12 is an enlarged perspective view of the trigger and advancer carriage components of the advancement gun shown in FIG. 8.

The advancement gun 65 includes a wafer advancement carriage 80 that is slidably disposed within an advancer channel 90 in the housings 67, 68, as shown in FIG. 11. The carriage 80 is connected to the lever arm 73 of the trigger 70 by way of a link 82. The link 82 is pivotably connected to the lever arm 73 and the carriage 80 by corresponding pivot pins 84, as depicted in FIGS. 11 and 12. As can be discerned from FIG. 11, when the trigger 70 is depressed, the lever arm 73 pivots in a clockwise direction, which pushes the link 82 against the carriage 80. Since the carriage is constrained within the channel 90, the pivoting movement of the trigger is translated to a linear movement of the carriage 80 toward the distal end 69 of the advancement gun 65. Each depression of the trigger constitutes one cycle of operation of the advancement gun, which corresponds to moving each wafer an incremental distance toward the discharge end 64 of the track assembly 63. This incremental distance is determined by the "throw" of the advancement gun, which in turn is related to the angle through which the trigger 70 can pivot within the gun. In the preferred embodiment, the throw of the advancement gun corresponds to a distance slightly greater than the length of a wafer.

Figure 9:
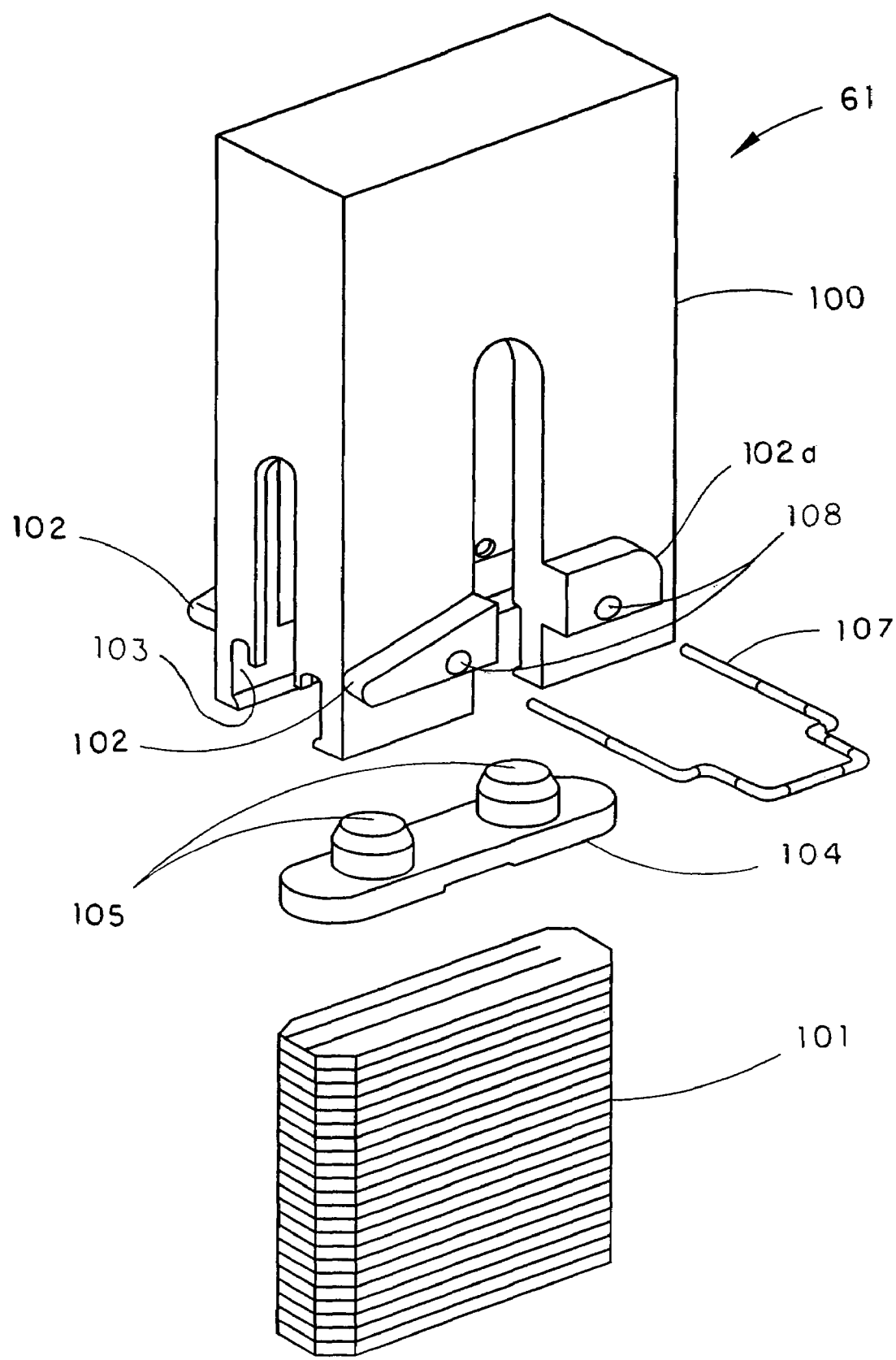
Figure 10:
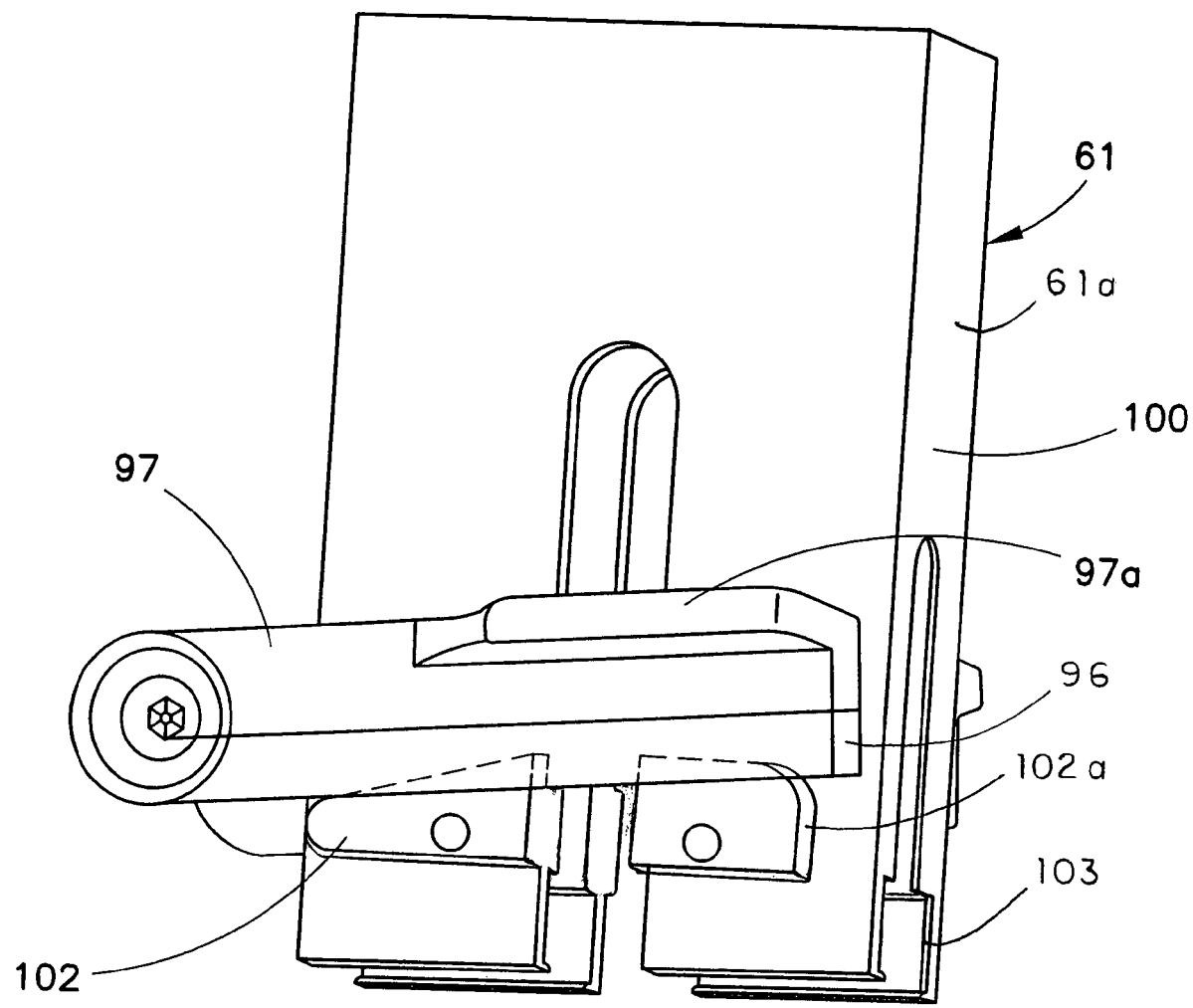
FIG. 10 is an enlarged view of the interface between the wafer cartridge component shown in FIG. 9 and a cartridge latch component of the wafer insertion apparatus shown in FIGS. 7 and 8.

The advancement gun 65 includes means for engaging a removable wafer cartridge, such as the cartridge 61. This feature allows a cartridge to be replaced while the apparatus is still in its operative position relative to the tissue surfaces being distracted. The distal end 69 of the advancement gun 65 defines engagement slots 95 that interface with locking cams 102 on opposite sides of the cartridge housing 100 (see FIG. 9). The cams 102 are configured to slide into the engagement slots 95. The advancement gun 65 includes latch halves 97 pivotably mounted to corresponding housing halves 67, 68 by a pivot pin 98 passing through a bore 99. The ends 96 of the latch halves 97 are turned inward to engage an end face 102a (FIG. 7) of the locking cams 102 on cartridge 61. When the latch ends engage the end face of the cartridge, they push the locking cams 102 into the slots 95. The latch halves can be provided with finger tabs 97a that can be pushed or pulled to engage or release the cartridge engagement means.

Referring again to FIG. 9, the cartridge 80 is shown with a housing 100 defining a cavity for receiving a stack of wafers 101. The cartridge can be provided pre-loaded so that the cartridge can be simply engaged to the advancement gun 65, and then removed and replaced once all the wafers have been discharged. The cartridge 61 can include a removable retainer clip 107 that spans the cavity in the housing 100 to hold the wafer stack 101 within the cartridge until it is needed. The arms of the clip 107 pass through openings 108 in the cartridge and underneath the stack 101. The retainer clip is kept in place as the cartridge is loaded in the advancement gun and then removed so that the stack 101 moves vertically into the gun.

In one embodiment, the cartridge 61 includes a spring plate 104 that is mounted on top of the stack 101. A spring arrangement (not shown) can be disposed between the spring plate 104 and the top of the housing 100 to provide pressure on the stack 101. The spring plate 104 can include a number of posts 105 configured to support the spring arrangement. The spring arrangement thus ensures that the lowermost wafer of the stack 101 is situated at the base of the cartridge during operation of the apparatus 60.

Turning back to FIGS. 8 and 11, the wafer advancement carriage 80 includes an advancer attachment notch 86 at its distal operating end. An attachment post 87 encroaches into the notch 86, as best seen in FIG. 12. The notch 86 and post 87 are provided for attaching an advancer or pusher 135 shown in FIG. 14. The pusher 135 includes an opening 139 at its proximal or engagement end 138. The engagement end 138 is configured to slide into the notch 86 of the carriage until the post 87 engages the opening 139 to lock the pusher 135 to the carriage 80.

Figure 8:
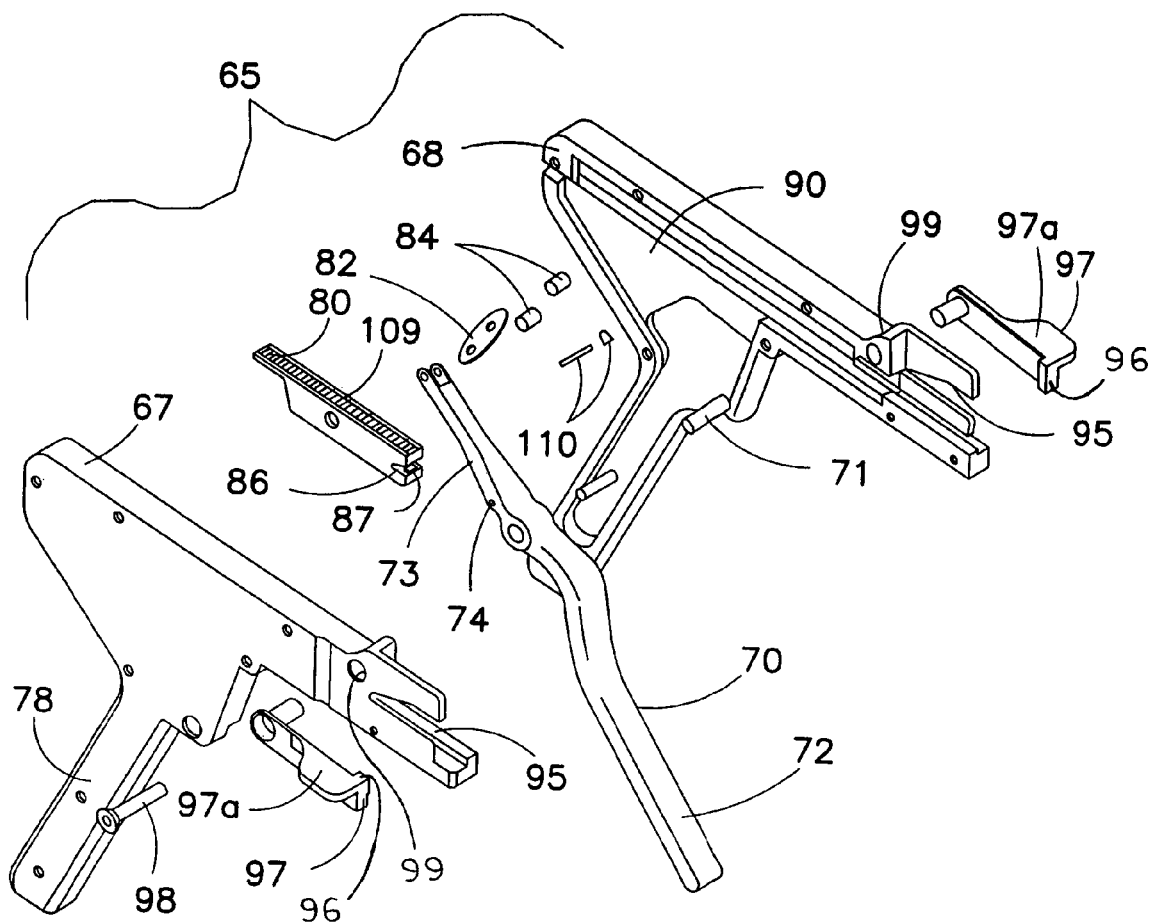
FIG. 8 is an exploded view of the advancement gun component of the wafer insertion apparatus shown in FIG. 7.

As also shown in FIGS. 8 and 12, the carriage 80 includes an upper ratchet face 109. This ratchet face 109 engages a full throw assembly 110 that is configured to ensure that the carriage 80 travels through its full stroke before being allowed to return to its starting position (such as by operation of the return spring 76 connected to the trigger 70). The full throw assembly 110 includes a ratchet clip 111 that engages the ratchet face 109 of the carriage as the carriage is advanced toward the distal end 69 of the advancement gun. Thus, as long as the ratchet face 109 is in contact with the clip 111, the carriage cannot move on its return stroke. Once the carriage has been advanced far enough toward the distal end 69 so that the ratchet face 109 is clear of the clip, the carriage can be drawn back to its initial position by the lever arm 73 and link 82, preferably by operation of the spring 76. This feature ensures that the trigger will be fully depressed and a wafer advanced through a full cycle of movement. Absent this feature, a partial depression of the trigger could cause the wafer insertion apparatus to jam as a partially advanced or partially loaded wafer gets lodged within the track assembly 63.

Figure 13:
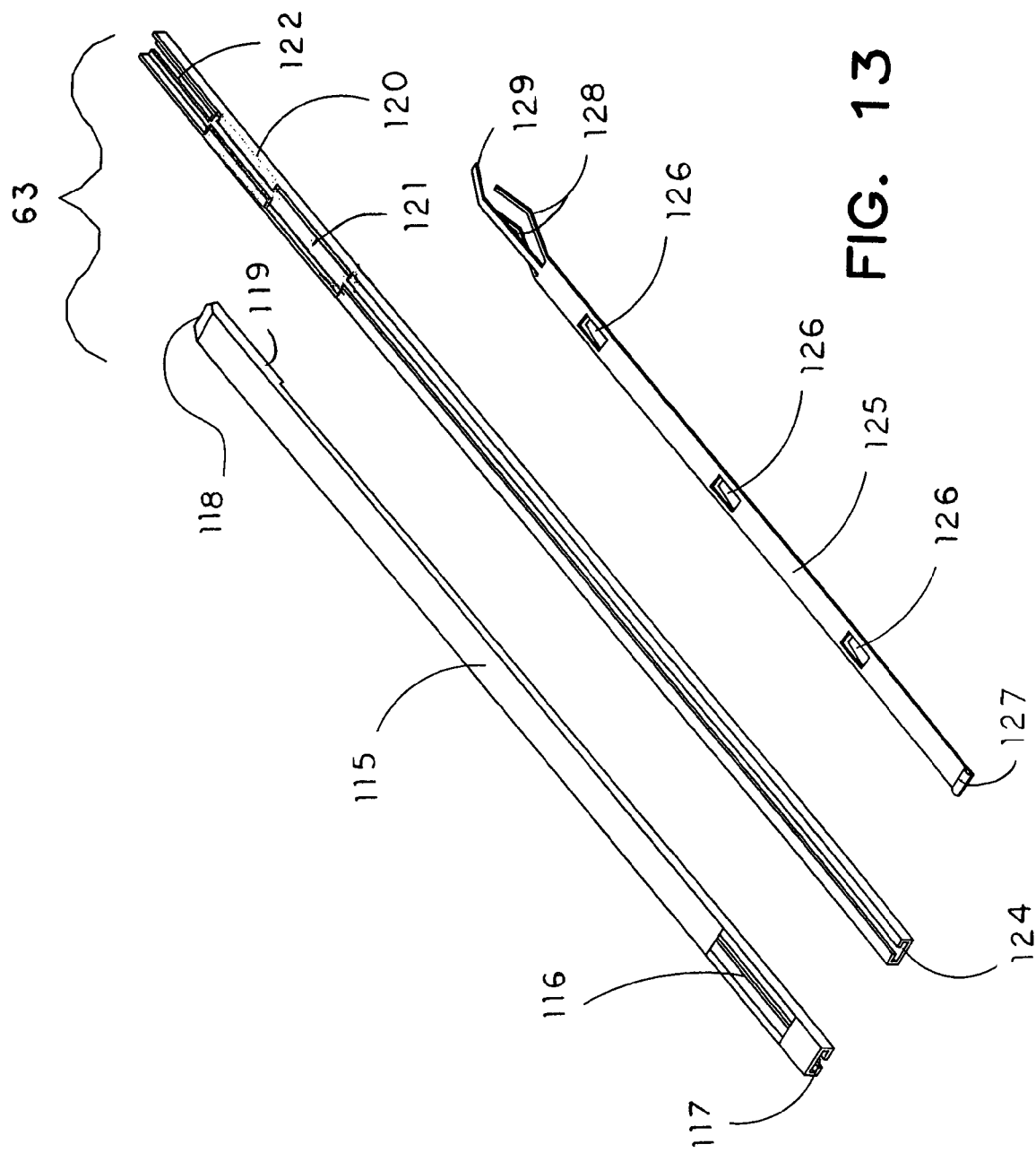
FIG. 13 is an exploded view of the track assembly component of the wafer insertion apparatus shown in FIG. 7.

Details of the track assembly 63 can be seen in FIG. 13. In the preferred embodiment, the track assembly 63 includes a top track 115, a bottom track 120 and a wafer stay 125. The track assembly 63 is mounted to the wafer cartridge 100, which is mounted to the distal end 69 of the advancement gun 65. In one embodiment, the end walls 61a of the wafer cartridge housing 100 define a slot 103 into which the track assembly 63 is mounted. The top track includes a wafer insertion opening 116 that is disposed immediately beneath the wafer stack 101 when the track assembly is mounted within the slot 103. The top track further defines a wafer channel 117 along its length that provides the initial path along which a succession of wafers can be advanced to the discharge end 64 (FIG. 7) of the apparatus. The end 118 of the top track is configured to engage the bottom track at a location 121. Preferably, the end 118 is configured at portion 119 to wrap around the bottom track at this location and can be suitably affixed so that the track assembly 63 is substantially rigid.

Figure 15:
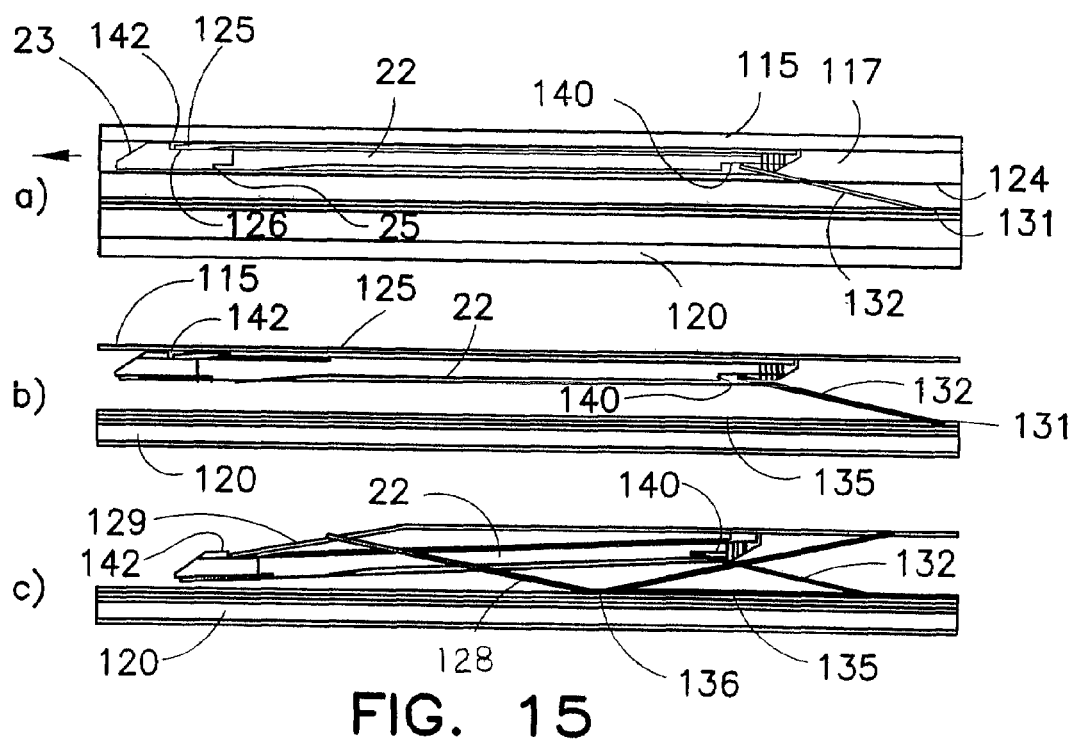
FIGS. 15(a)-15(c) are side partial views of the advancer/pusher shown in FIG. 14 mounted within the track assembly shown in FIG. 13 in different stages of operation to advance a wafer along the track assembly.

The channel 117 of the top track 115 retains the wafer stay 125, which functions to hold wafers within the channel 117 as the advancer/pusher mechanism 92 follows its return stroke (as explained below). A tab 127 at the proximal end of the wafer stay engages the distal end of the wafer insertion opening 116 to hold the stay in place. The wafer stay 125 includes a series of substantially evenly spaced intermediate prongs 126. The prongs 126 project downward at an angle into the wafer channel 117, facing the discharge end 64, as illustrated in FIG. 15(a). With this orientation, the prongs 125 do not impede forward movement of wafers along the channel. However, the prongs prevent retrograde movement since the free end of the prongs contact the back end of a wafer as it moves backward in the channel. Preferably, prongs 126 of the wafer stay 125 are formed of a material that is sufficiently firm to resist this retrograde movement, yet sufficiently flexible to deflect upward as a wafer passes underneath. For example, the prongs, as well as the entire wafer stay, may be formed of a thin gage stainless steel.

Again referring to FIG. 13, the bottom track 120 defines a pusher channel 124 that receives the advancer/pusher mechanism 92 (FIGS. 7 and 14) for reciprocating linear motion. The top track 115 is configured to overlie the bottom track 120 and engages the bottom track at the engagement end 118, as described above. It should be noted that the engagement end 118 is configured to provide an exit opening for a wafer that has traveled the length of the top track. The wafer thus exits the top track and drops into the bottom track 120 at the introduction slot 121.

In one aspect of the invention, the wafer stay 125 is configured to assist in this track change. In particular, in a preferred embodiment, the distal end of the wafer stay includes a pair of opposite spaced apart leaf springs 128. These leaf springs help maintain the wafer stay 125 within the top track 115 and also help keep the wafers in a proper orientation for entry into the introduction opening 121 of the bottom track, as best illustrated in FIG. 15(c). The wafer stay 125 also includes a dislodgement leaf spring 129 that is angled downward toward the bottom track. As a wafer moves toward the discharge/engagement end 118, the dislodgement leaf spring 129 pushes the wafer down into the introduction opening 121 of the bottom track 120. Once the wafer is within the bottom track, the pusher (FIG. 14) can be used to advance the wafer to the wafer discharge opening 122 of the bottom track 120. As explained above, this discharge opening is situated within the body space to be distracted.

Figure 14:
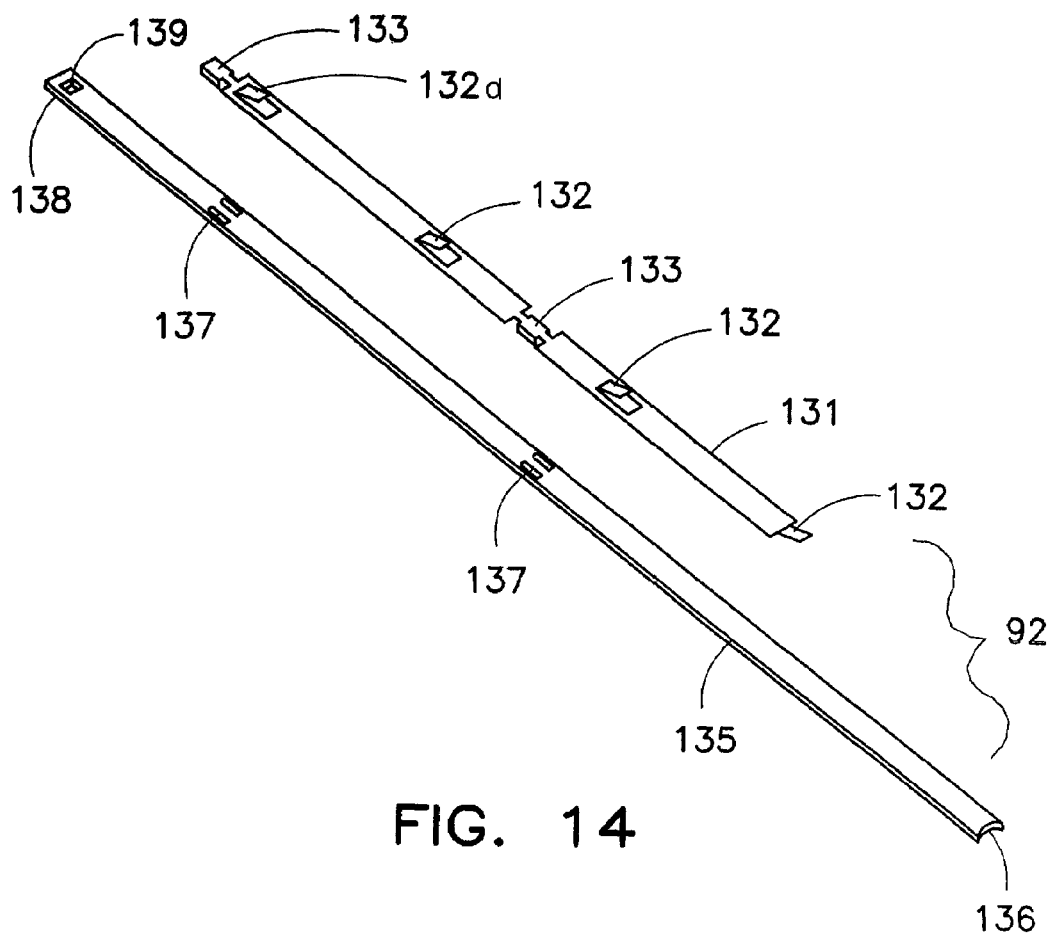
FIG. 14 is an exploded view of an advancer/pusher assembly for use with the wafer insertion apparatus shown in FIG. 7.

Details of the advancer/pusher mechanism 92 can be seen in FIG. 14. The mechanism includes an advancer 131 that includes a series of substantially evenly spaced fingers 132. These fingers project upward into the top track 115 when the advancer/pusher mechanism is disposed within the channel 124 in the bottom track 120, as shown in FIG. 15(b). Like the wafer stay 125, the fingers 132 on the inserter 131 are angled forward. This forward sweep of the fingers allows the inserter 131 to be retracted without pulling a wafer backward with it. As with the wafer stay, the fingers 132 are preferably spaced apart a distance slightly greater than the length of a wafer. In this way, the length of the tracks can be minimized and the regularity of the wafer insertion can be maintained.

The advancer 131 includes attachment clips 133 that engage attachment slots 137 in the pusher 135. Thus, the advancer 131 and pusher 135 are coupled and move together within the channel 124 of the bottom track. However, unlike the advancer, the pusher 135 essentially only operates on a wafer that is within the discharge opening 122 of the bottom channel. Thus, the pusher 135 includes a pusher end 136 that is configured to engage the proximal end of a wafer. The opposite end of the pusher defines an engagement end 138 and opening 139 that engage the wafer advancement carriage 80 as described above.

The operation of the track assembly 63 and advancer/pusher mechanism 92 can be understood from consideration of FIGS. 15(a)-(c). In FIG. 15(a), a wafer 22 is shown within the wafer channel 117 of the top track 115. The wafer includes a leading beveled end 23 that facilitates introduction of the wafer 22 underneath a previously advanced wafer disposed at the distraction site. The proximal end of the wafer preferably defines an advancement notch 140 that can be engaged by the wafer advancer 131 and the pusher 135. As shown in FIGS. 15(a)-(b), a finger 132 of the advancer 131 engages the notch 23 of the wafer 22 to push it along the top track 115 toward the distraction site. A prong 126 of the wafer stay 125 is also shown in FIG. 15(a), wherein the prong is deflected upward to allow passage of the wafer.

In one embodiment of the invention, the wafer 22 can be provided with a notch 142 at its leading end. Prongs 126 of the wafer stay 125 can resiliently drop into the notch 142 as the leading end of the wafer advances to prevent retrograde movement of the wafer. In the illustrated embodiment of FIG. 13, the wafer stay includes four prongs 126 to engage the notch 142 of three wafers situated within the wafer channel 117. In the illustrated embodiment, the prongs 126 are spaced along the top track by a distance slightly greater than the length of a wafer. Alternatively, a greater number of prongs can be provided, with the understanding that when the wafers sit within the wafer channel at the end of a stroke some prongs will engage the retrograde notches 142 of the wafers while other prongs will be resiliently compressed by the wafers.

As the wafer moves toward the engagement end 118 of the top track, the dislodgement leaf spring 129 of the wafer stay 125 contacts the wafer, as shown in FIG. 15(c). The spring 129 pushes the wafer downward into the bottom track 120. It can be seen in FIG. 15(c) that the pusher 135 is beneath the wafer. Once the wafer is disposed within the introduction opening 121 of the bottom track 120, the end 136 of the pusher can then contact the advancement notch 23 of the wafer. The advancer/pusher mechanism 92 is propelled toward the discharge end 64 of the apparatus, so the pusher end 136 continues to push the wafer until it is firmly positioned at the bottom of the distraction stack.

As should be apparent, the advancer/pusher mechanism 92 (including the connected advancer 131 and pusher 135) moves in the pusher channel 124 of the bottom track 120 relative to the stationary wafer stay 125, which is fixed within the wafer channel 117 of the top track 115. Thus, as the advancer/pusher mechanism 92 is retracted, the fingers 132 of the wafer advancer 131 slide along the bottom of the wafers remaining in the wafer channel 117 until the wafer advancement carriage 80 reaches the end of its return stroke. At this point, the rearmost prong 132a is situated beneath the wafer cartridge 61. A wafer from the stack 101 that has fallen into the opening 116 in the top track 115 is engaged by the finger 132a. When the trigger 70 is depressed again, the carriage 80 propels the advancer/pusher mechanism 92 to simultaneously propel one wafer into the wafer discharge opening 122 of the bottom track 120 and other wafers within the top track along the wafer channel 117. This procedure is repeated until the stack of wafers has been fully formed within the distracted body.

Figure 16:
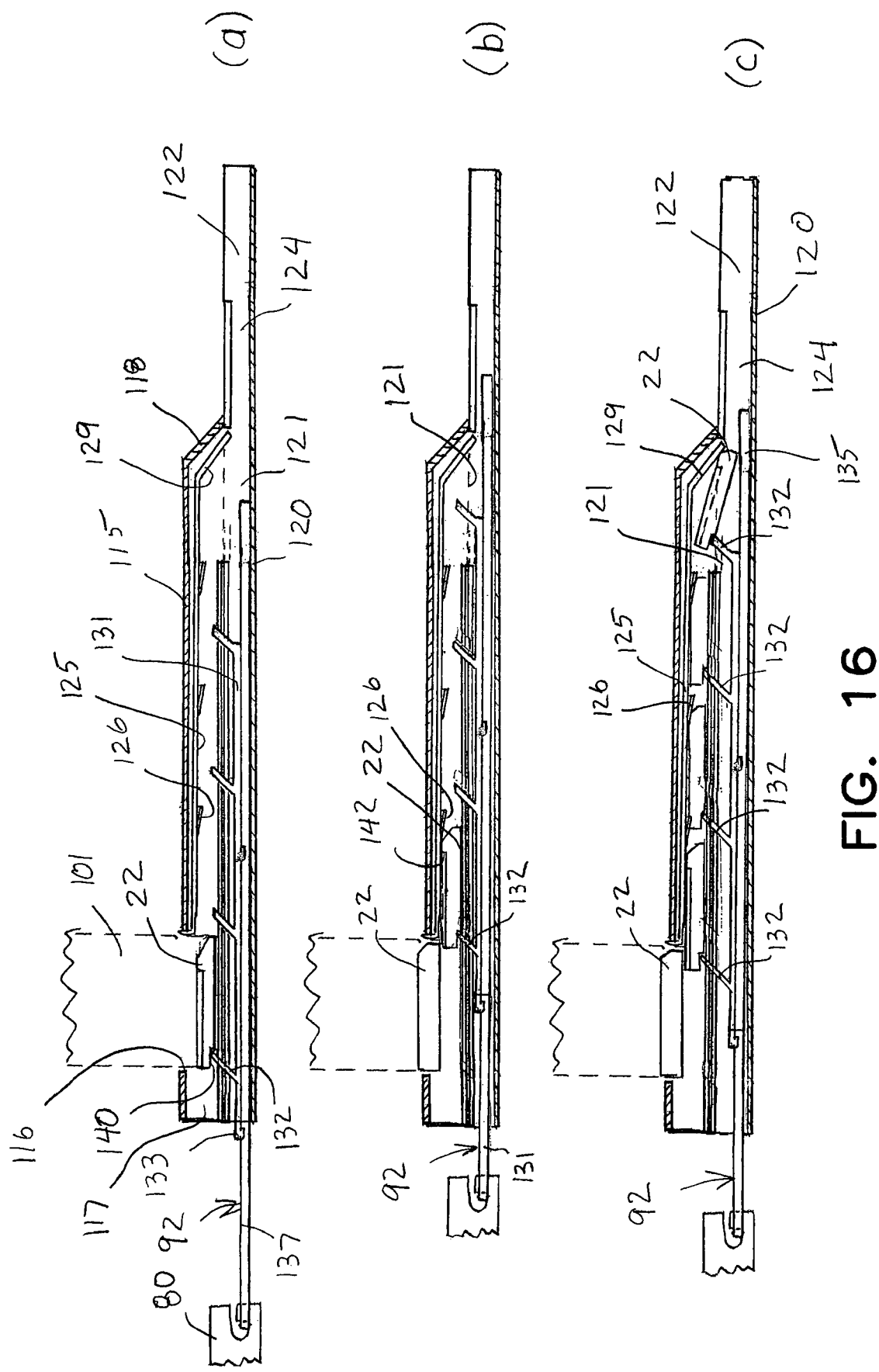
FIGS. 16(a)-(c) are side views of the apparatus depicting various stages of advancement of a wafer to the discharge end.

A sequence of events in the use of the insertion apparatus 60 is depicted in FIGS. 16(a)-(c). When the apparatus 60 is initially actuated, a wafer 22 is situated at the bottom of the wafer stack 101 within the wafer channel 117, as shown in FIG. 16(a). The advancement notch 140 of the wafer is engaged by a finger 132 of the wafer advancer 131. The remainder of the wafer channel 117 is empty. As the wafer advancement carriage 80 is translated forward (by depressing the trigger 70 of the advancement gun 65), the carriage pushes the wafer advancer 131, and ultimately the finger 132 advances the wafer along the top track 115, as shown in FIG. 16(b).

The wafer advancer 131 is shown near the end of its stroke in FIG. 16(b). When the advancer has been fully advanced, the wafer 122 is caught by the first prong 126 of the wafer stay 125. The advancer is then retracted with the carriage 80 until the advancer 131 is aligned under the wafer stack 101, as depicted in FIG. 16(a). The next wafer has already dropped through the opening 116 in the top track 115 and is awaiting engagement by the finger 132. The above steps are repeated and with each successive depression of the trigger the wafers 22 advance to the next prong 126 of the wafer stay.

On the fourth actuation of the advancement gun 65, the initial wafer 22 is in the position shown in FIG. 16(c). As explained above, the dislodgement prong 129 directs the wafer from the wafer channel 117 in the top track 115 to the pusher channel 124 in the bottom track 120. As the pusher 135 is retracted, the wafer is held in place within the wafer introduction slot 121. When the advancer/pusher mechanism 92 is fully retracted, the pusher 135 engages the advancement notch 140 in the lead wafer. Subsequent activation of the gun 65 causes the pusher 135 to propel the wafer into the discharge opening 122.

In the embodiment illustrated in FIGS. 7-16, the wafers are introduced into the body cavity from the bottom of the wafer stack. In other words, with this embodiment, each successive wafer pushes the previously stacked wafers upward to distract the space. In an alternative embodiment, the wafers are stacked in the opposite direction. Thus, a wafer insertion apparatus 150 shown in FIGS. 17-18 includes an advancement gun 152 and a wafer cartridge supported on the underside of the gun. The track assembly 156 is supported by the gun. The gun includes a trigger 158 that reciprocates a wafer advancement carriage 160 engaged to an advancement/pusher mechanism 162. All of these components can be configured similar to the prior embodiments, except that they are modified to advance each wafer onto the top of the stack within the body cavity.

Figure 17:
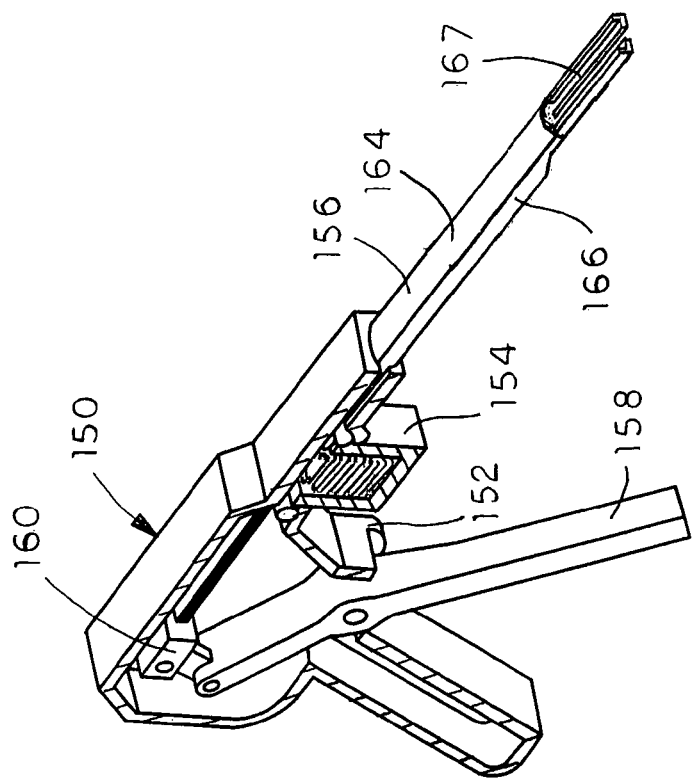
FIG. 17 is perspective cut-away view of a wafer insertion apparatus according to a further embodiment of the invention.

The track assembly 156 includes a top track 164 and a bottom track 166 that are essentially the analog of the bottom track 120 and top track 115, respectively, of the previous embodiment. Thus, each wafer exits the apparatus 150 from a discharge opening 167 in the bottom track 166. The moving components of the apparatus 150 can be configured similar to the like components of the previous embodiment, except that components of the apparatus 150 of FIGS. 17-18 are switched between the top and bottom tracks from those in the apparatus 60.

Figure 18:
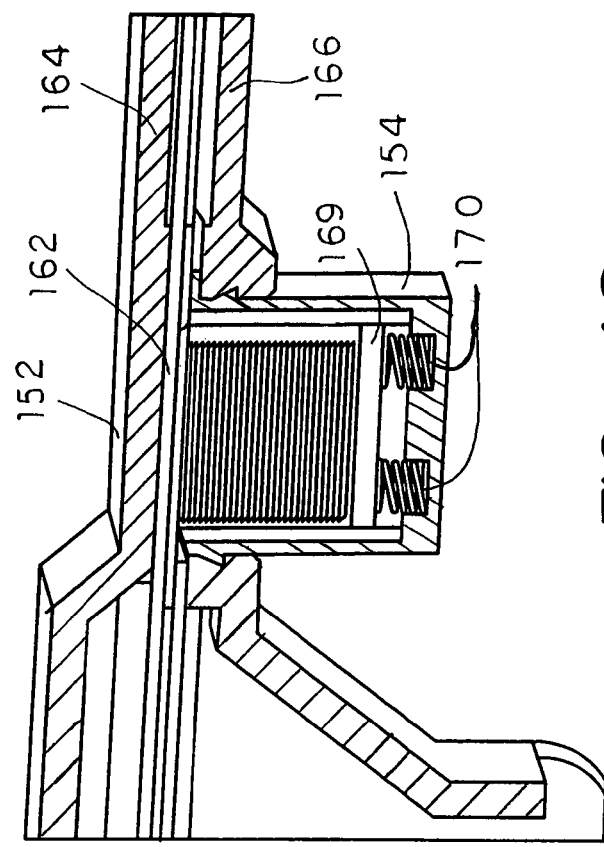
FIG. 18 is a side cross-sectional view of the wafer cartridge portion of the apparatus shown in FIG. 17.

As shown in FIG. 18, the wafer cartridge 154 is mounted to the underside of the advancement gun 152. Thus, each wafer is fed upward into the bottom track 166 and into engagement with the advancement/pusher mechanism 162. In order to drive the stack into the advancement mechanism, a spring plate 169 is biased upward into the wafer stack by an arrangement of springs 170. This arrangement is similar to the spring biased stack described above in connection with the apparatus 60.

Figure 19:
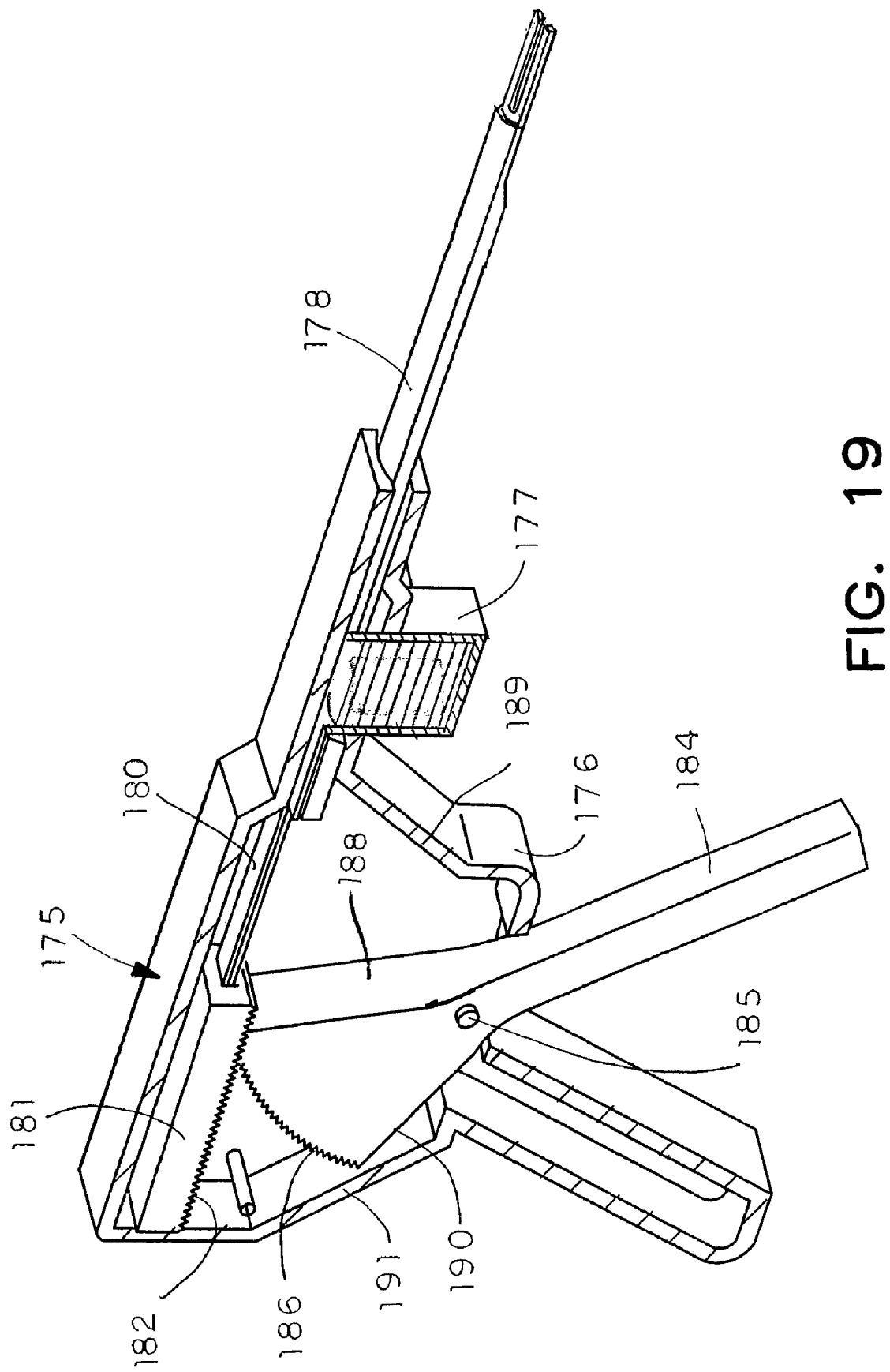
FIG. 19 is a perspective cut-away view of a wafer insertion apparatus according to a further embodiment of the invention.

The present invention contemplates a trigger driven advancement/pusher mechanism, such as the mechanism 92 described above. In the previous embodiments, the trigger, such as trigger 70, is connected to a carriage 80 by a floating link 82. Other trigger or actuation mechanisms are contemplated by the invention. For example, in one alternative embodiment, a wafer insertion apparatus 175 includes an advancement gun 176, a bottom loaded cartridge 177 and a track assembly 178, as shown in FIG. 19. An advancement/pusher mechanism 180 is engaged to a carriage 181 that is slidably disposed in the gun, in a fashion similar to the embodiments described above.

The gun further includes a trigger 184 that is pivotably engaged to the gun at a pivot mount 185. In this embodiment, the carriage 181 includes a rack gear 182 facing the trigger. The trigger 184 includes a clock gear 186 that meshes with the rack gear 182 as the trigger is pivoted. Thus, the drive interface between the trigger and the carriage is direct, without any intermediate linkage structure.

In a further aspect of this embodiment, the trigger 184 defines a stop face 188. This stop face contacts a stop wall 189 of the advancement gun 176 to prevent further pivoting of the trigger. More significantly, when the trigger can no longer pivot, the translation of the carriage 181 stops, signifying the end of the stroke of the advancement/pusher mechanism 180. With this feature, the full throw assembly 110 (FIG. 8) can be eliminated. Similarly, the back face 190 of the trigger 184 can contact a rear stop wall 191 to limit the return movement of the trigger, and therefore the carriage.

Figure 20:
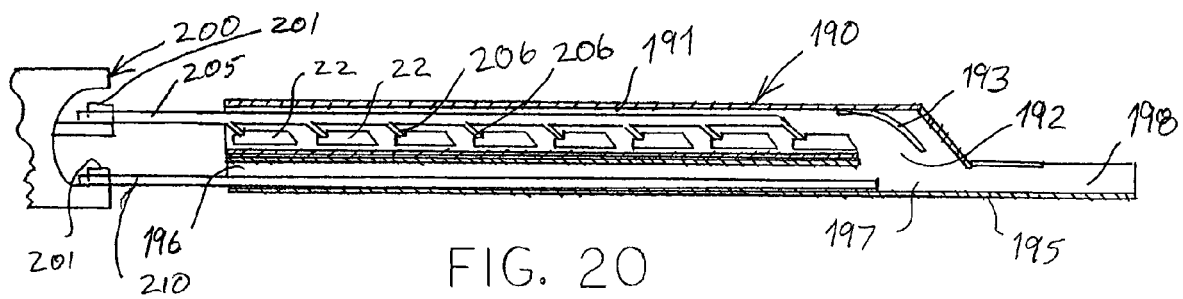
FIG. 20 is a side partial cross-sectional view of a wafer insertion apparatus with a modified wafer cartridge according to an additional embodiment of the invention.

In the embodiments disclosed above, the wafer cartridge is oriented to form a vertical stack of new wafers to be introduced into the body cavity. In an alternative embodiment, the wafer cartridge can provide the wafers in a horizontal arrangement, as depicted in FIG. 20. In this embodiment, the top track is essentially replaced by a cartridge 190 that is mounted on the single track 195. The wafers 22 are provided in a row within the wafer channel 191 of the cartridge, essentially spanning the length of the track 195. The wafer channel is provided with an opening 192 that mates with a wafer introduction slot 197 in the track 195. A deflection prong 193 is mounted within the channel and performs essentially the same function as the dislodgement spring 129 of the previous embodiments—i.e., to direct the leading wafer into the track 195.

In this embodiment, a wafer advancer 205 is disposed in the wafer channel 201 of the cartridge. Fingers 206 on the wafer advancer engage the back end of the wafers to push the wafers along the channel as the advancer is reciprocated. As with the wafer advancer 131, the fingers 206 can be flexible to retract as the advancer is withdrawn from the end of its stroke.

Figure 21:
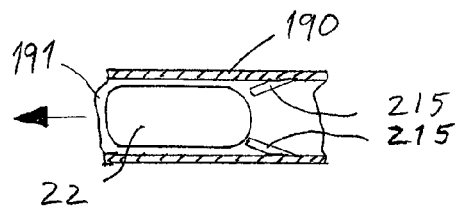
FIG. 21 is an enlarged view of a portion of the apparatus shown in FIG. 20.

In order to maintain the position of the wafers 22 during the return stroke of the advancer 205, the cartridge 190 can be provided with spring fingers 215 on opposite sides of the channel 191, as shown in FIG. 21. The fingers 215 are arranged at an angle toward the direction of travel of the wafers so that they retract as a wafer passes. However, retrograde movement of the wafers causes them to contact the spring fingers 215 and push them into the middle of the channel 191, thereby preventing further retrograde travel of the wafers.

Returning to FIG. 20, the apparatus also includes a pusher 210 disposed in the pusher channel 196 of the track 195. Unlike the prior embodiments, the pusher 210 is separate from the wafer advancer 205. The pusher 210 and the advancer 205 can be engaged to posts 201 on a modified carriage 200. The carriage can be driven in any of the manners described above. It can be appreciated that when the carriage 200 translates it propels the wafer advancer 205 and pusher 210 toward the discharge end 198. The wafers are advanced and discharged in substantially the same manner as the embodiments described above.

Figure 22:
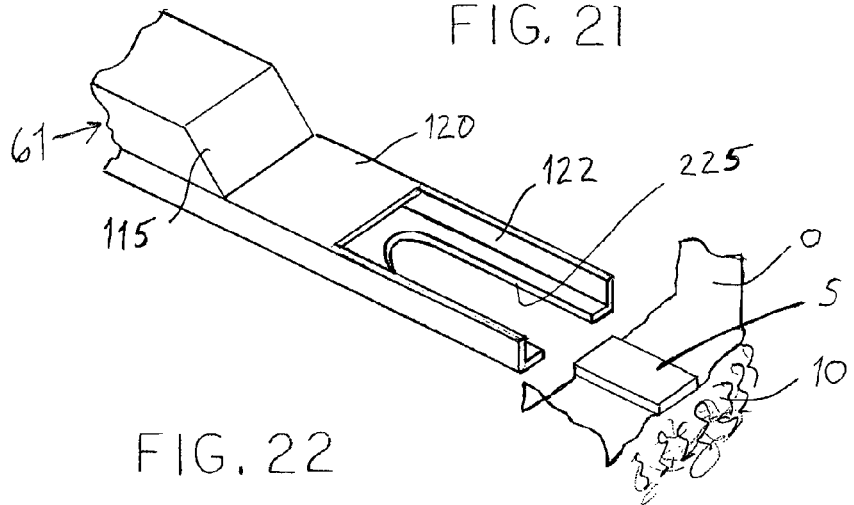
FIG. 22 is an enlarged perspective view of the discharge end of the apparatus shown in FIG. 7

In a further feature of the invention, the apparatus can be provided with means for interfacing with a vertebral body to help stabilize the apparatus. In particular, the bottom track 120 of the assembly 61 illustrated in FIG. 7 can be configured to mate with features formed in the cortical bone of a vertebral body. As shown in FIG. 22, the apparatus 61 is introduced into an opening O in a vertebral body 10. In this instance, as discussed in the '998 patent incorporated by reference, the wafers are used to distract and restore the height h of a vertebral body 10 (see FIG. 2). The opening O thus provides access to the cancellous bone of the vertebral body. The opening O can be prepared using a bone working tool such as a drill. In order to help guide the wafer insertion apparatus 61, the base of the opening can be formed with a step S. The step is configured to be engaged by a slot 225 in the discharge opening 122 of the bottom track 120. With the slot 225 engaging the step S the discharge end of the apparatus is stabilized as the wafers are introduced.

While a preferred embodiment of the present invention has been described, it should be understood that various changes, adaptation and modification may be made therein without departing from the spirit of the invention and the scope of the appended claims.

What is claimed is:

1. An apparatus for sequentially inserting wafers into a body space of a patient, the apparatus comprising:
    a track assembly defining a channel from an introduction end configured to receive wafers, to an opposite discharge end adapted to be positioned within the body space, said channel configured to sequentially receive the plurality of wafers therein and including;
        a first track defining a wafer channel having an opening at said introduction end sized and configured to receive wafers therethrough; and
        a second track coupled to said first track and defining a pusher channel;
    a cartridge carrying a plurality of wafers, said cartridge coupled to said track assembly at said wafer channel opening so that a wafer from said plurality of wafers enters said introduction end of said track assembly through said wafer channel opening;
    an advancement mechanism slidably disposed within said pusher channel of said track assembly and operable on a wafer within said wafer channel to advance the wafer in a first direction along said wafer channel toward said discharge end;
    means for preventing retrograde movement of a wafer within said wafer channel in a second direction opposite said first direction;
    an advancement gun supporting said track assembly and having a manually operable trigger operably coupled to said advancement mechanism so that depressing said trigger slides said advancement mechanism in said first direction within said pusher channel; and
    a pair of locking cams disposed on said cartridge and a pair of latches pivotably mounted to said advancement gun and pivotable to engage said pair of locking cams to removably mount said track assembly, with said cartridge coupled thereto, to said advancement gun.

2. The apparatus of claim 1, wherein:
said advancement gun includes a housing; and
said trigger is pivotably mounted within said housing.

3. The apparatus of claim 2, wherein:
said advancement mechanism includes a rack gear; and
said trigger includes a clock gear arranged to mesh with said rack gear as said trigger is pivoted.

4. The apparatus of claim 1, wherein
said means for preventing retrograde movement includes a plurality of resilient prongs spaced along the length of said track assembly channel from said introduction end to said discharge end, said plurality of resilient prongs being provided in opposing pairs of prongs disposed on opposite sides of said track assembly channel.

5. The apparatus of claim 1, wherein said advancement mechanism includes at least one finger projecting from said portion into said wafer channel to push a wafer disposed within said wafer channel.

6. The apparatus of claim 1, wherein
said track assembly includes means for diverting a wafer from said wafer channel into said pusher channel as the wafer is conveyed along said wafer channel.

7. The apparatus of claim 6, wherein said means for diverting includes a spring arm mounted within said wafer channel and arranged to guide a wafer from said wafer channel to said pusher channel.

8. The apparatus of claim 1, wherein said advancement gun includes a linkage coupled to said trigger and configured to engage said advancement mechanism when said track assembly is mounted to said gun, said linkage configured to translate pivoting of said trigger into linear movement of said mechanism within said pusher channel.

9. An apparatus for sequentially inserting wafers into a body space of a patient, the apparatus comprising:
a track assembly defining a channel from an introduction end configured to receive wafers, to an opposite discharge end adapted to be positioned within the body space, said channel configured to sequentially receive the plurality of wafers therein and including;
a first track defining a wafer channel having an opening at said introduction end sized and configured to receive wafers therethrough; and
a second track coupled to said first track and defining a pusher channel;
a cartridge carrying a plurality of wafers, said cartridge coupled to said track assembly at said wafer channel opening so that a wafer from said plurality of wafers enters said introduction end of said track assembly through said wafer channel opening;
an advancement mechanism slidably disposed within said pusher channel of said track assembly and operable on a wafer within said wafer channel to advance the wafer in a first direction along said wafer channel toward said discharge end;
means for preventing retrograde movement of a wafer within said wafer channel in a second direction opposite said first direction;
an advancement gun supporting said track assembly and having a manually operable trigger operably coupled to said advancement mechanism so that depressing said trigger slides said advancement mechanism in said first direction within said pusher channel; and
a pair of locking cams disposed on said cartridge and a pair of latching surfaces on said advancement gun to engage said pair of locking cams to removably mount said track assembly, with said cartridge coupled thereto, to said advancement gun.

10. An apparatus for sequentially inserting wafers into a body space of a patient, the apparatus comprising:
a track assembly defining a channel from an introduction end configured to receive wafers, to an opposite discharge end adapted to be positioned within the body space, said channel configured to sequentially receive the plurality of wafers therein and including;
a first track defining a wafer channel having an opening at said introduction end sized and configured to receive wafers therethrough; and
a second track coupled to said first track and defining a pusher channel;
a cartridge carrying a plurality of wafers, said cartridge coupled to said track assembly at said wafer channel opening so that a wafer from said plurality of wafers enters said introduction end of said track assembly through said wafer channel opening;
an advancement mechanism slidably disposed within said pusher channel of said track assembly and operable on a wafer within said wafer channel to advance the wafer in a first direction along said wafer channel toward said discharge end;
at least one resilient prong arranged within said track assembly channel to prevent movement of a wafer in said second direction opposite said first direction and to deflect as a wafer passes said prong in said first direction;
an advancement gun supporting said track assembly and having a manually operable trigger operably coupled to said advancement mechanism so that depressing said trigger slides said advancement mechanism in said first direction within said pusher channel; and
a mounting mechanism to removably mount said track assembly, with said cartridge coupled thereto, to said advancement gun.

11. The apparatus of claim 10, wherein said mounting mechanism comprises a pair of locking cams disposed on said cartridge and a pair of latching surfaces on said advancement gun to engage said pair of locking cams.

12. The apparatus of claim 10, wherein there are a plurality of resilient prongs spaced along the length of said track assembly channel from said introduction end to said discharge end, said plurality of resilient prongs being provided in opposing pairs of prongs disposed on opposite sides of said track assembly channel.

* * * * *